United States Patent [19]

Harjunmaa

[11] Patent Number: 4,661,711
[45] Date of Patent: Apr. 28, 1987

[54] FLUOROMETER

[75] Inventor: Hannu Harjunmaa, Makslahdentie, Finland

[73] Assignee: Labsystems Oy, Helsinki, Finland

[21] Appl. No.: 765,059

[22] Filed: Aug. 12, 1985

[30] Foreign Application Priority Data

Aug. 29, 1984 [FI]  Finland ................... 843409

[51] Int. Cl.⁴ .......................................... G01N 21/64
[52] U.S. Cl. .............................. 250/458.1; 250/459.1; 250/252.1; 356/417
[58] Field of Search ............... 250/458.1, 459.1, 461.1, 250/461.2, 252.1; 356/317, 318, 243, 417

[56] References Cited

U.S. PATENT DOCUMENTS 4,161,656  7/1979  Marcuse et al. ................. 250/459.1
4,320,970  3/1982  Dowben et al. .................... 356/417
4,407,964  10/1983  Elings et al. ........................ 356/318

Primary Examiner—Carolyn E. Fields
Attorney, Agent, or Firm—Hopgood, Calimafde, Kalil, Blaustein & Judlowe

[57] ABSTRACT

Fluorometer in whose reference channel (5) there is optical fiber made of a fluorescent material. The optical fiber acts as an internal standard.

4 Claims, 1 Drawing Figure

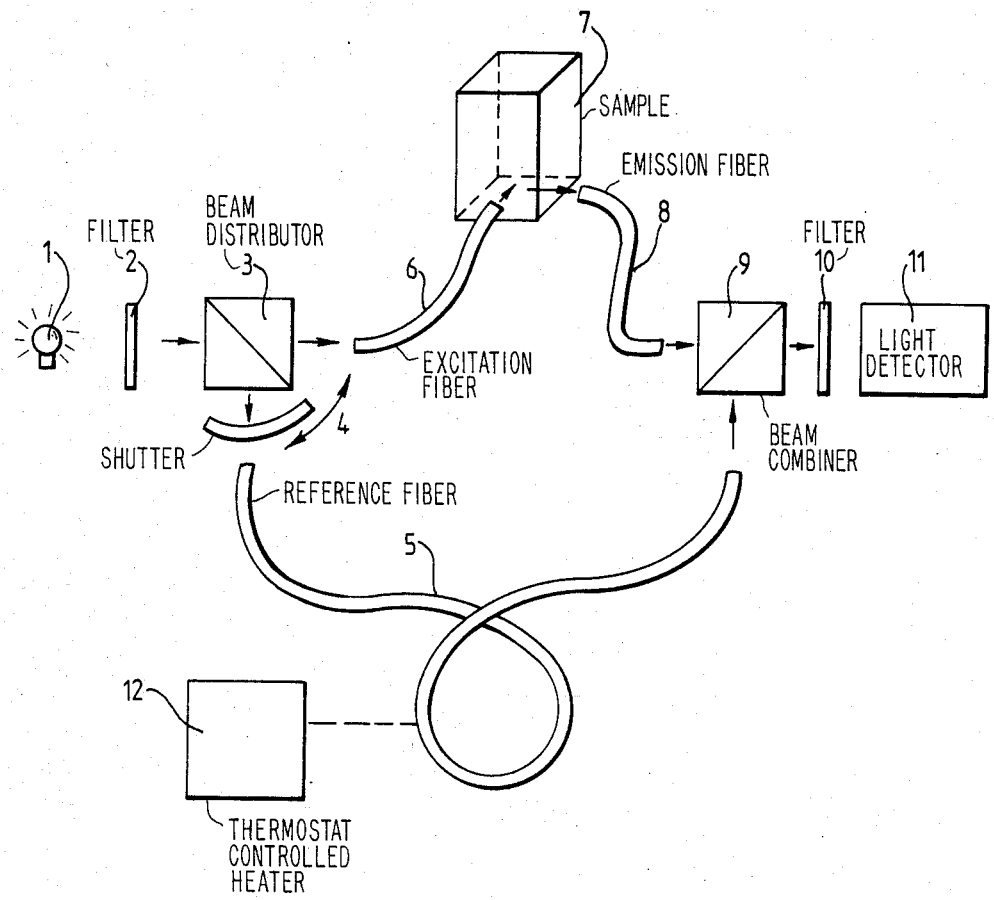

FLUOROMETER

The present invention is concerned with a measurement arrangement for the measurement of the fluorescence of a liquid, solid or gaseous sample, in which said arrangement any errors derived from variations in the brightness of the source of light and in the sensitivity of the light detector are eliminated by making use of an internal fluorescence standard.

By fluorescence is meant a phenomenon in which a substance, which is illuminated by means of a light, of a certain wavelength, radiates light of a longer wavelength. In a simple fluorometer, there is a source of light, a device for choosing the wavelength band of the light, a place where the sample is placed, and a light detector. The device for choosing the wavelength band of the light may be, e.g., a grating or prism monochromator or a filter. For the sake of simplicity, it is possible to speak of filters only. The light applied to the sample is called excitation light, and the light radiated by the sample itself emission light. By means of choice of the mutual geometric relationship between the excitation light beam and the system of collection of the emission light, attempts are mostly made to reach such a situation that a minimum of excitation light has access into the system of collection of the emission light and, through that system, to the detector. In spite of this, a little quantity of excitation light has access into the emission channel by the effect of scattering and reflections, so that, if very little quantities of fluorescent substance are to be measured, a filter must also be used in the emission channel.

In the brightness of the lamp, both long-term deterioration and short-term variations occur. Nor is the sensitivity of the detector, in particular of the multiplier phototube, constant but depends, e.g., on the temperature. In a spectrometer in which only one wavelength is used at a time, the effect of these phenomena on the measurement result can be eliminated simply by, at intervals of time, passing some of the monochromated light past the sample to the light detector and by using the signal obtained from this as a reference, or by adjusting the brightness of the lamp or the sensitivity of the multiplier phototube so that the said signal remains constant. In a fluorometer, in which the excitation light and the emission light are of different colours, stabilization cannot be arranged completely in an equally simple way. The temperature coefficient of the sensitivity of the multiplier phototube is, viz., different at different wavelengths: when the temperature rises, the sensitivity decreases almost within the entire wavelength range, except right at its end with the longest wavelengths, where it increases. Now, if excitation light passing past the emission filter to the multiplier phototube is used as the reference light, on an increase in the temperature the reference signal indicates that the sensitivity of the multiplier phototube has decreased, even though it has increased at the factual measurement wavelength. On the other hand, the excitation light cannot be passed to the multiplier phototube through the emission filter, because the emission filter is non-transparent at the excitation wavelength. The only means of providing complete stabilization while also considering any changes in the properties of the filters is the use of a fluorescence standard.

In prior art, the applying of the excitation light to the fluorescence standard and the collecting of the emission light from same have taken place substantially in the same way as in the case of a sample. This has required several lenses and other optical components or, if the same optical system has been used for the measurement of the sample and of the fluorescence standard, moving parts for the displacement of the sample and the fluorescence standard, or of the optical system.

In prior art, the apparatuses making use of an internal fluorescence standard have also been complicated and expensive. The fluorescence standard has been a water solution of a fluorescent chemical, which must be replaced at specified intervals, or a fluorescent chemical cast in plastic. As a rule, in the same solution there is only one fluorescent chemical, whereby the fluorescence standard can be used only at the wavelengths at which the chemical concerned fluoresces.

In simple fluorometers intended for routine operation, the effect of the variations in the intensity of the lamp and in the sensitivity of the detector on the measurement results has been compensated only partly, as is the case, e.g., in the "FLUOROSKAN" fluorometer of Messrs. EFLAB OY, wherein a separate reference detector is used for monitoring the variations in the brightness of the lamp, or in the "FIAX" fluorometer of IDL (see GB Patent Specification no. 1596 521), wherein the lamp light that has passed through a filter is passed by means of an interrupter, alternatingly with the measurement light, to a multiplier phototube.

The object of the present invention is to provide a fluorometric apparatus and method employing an internal fluorescent standard to eliminate errors in measurement effect of variations in the brightness of the excitation lamp and in the sensitivity of the emission detector.

The essential novelty of the present invention is that the optical system, along which the monochromated reference light is passed to the emission monochromator, from where it passes to the light detector, comprises an optical fiber or bundle of fibers which is made of an appropriately fluorescent material, such as plastic, and, thus, acts simultaneously both as a conductor of light and as a fluorescence standard.

The apparatus in accordance with the present invention includes a beam distributor, as do many other apparatuses that employ a reference channel, but the reference light obtained from the beam distributor is immediately fed into an optical fiber, which is made, exclusively or partly, of an appropriate material, e.g. plastic, which fluoresces within the wavelength range of the light detector when it is illuminated at any of the excitation wavelengths in use. The light coming from the other end of this optical fiber, which said fiber is here called the reference fiber, and which actually may be a bundle of fibers, is passed through an emission filter to the light detector. Since the fluorescence of the sample is always compared with the fluorescence of the reference fiber, which is constant, the result is independent from the brightness of the lamp or from the sensitivity of the detector.

In accordance with the invention, it is possible to provide a fluorometer employing an internal fluorescence standard which is remarkably more simple as compared with the apparatuses known in prior art.

One fluorometer in accordance with the present invention is illustrated in the attached FIGURE.

The light source is a lamp 1. An excitation filter 2 separates an appropriate excitation wavelength band from the light. The beam distributor 3 divides the light to the measurement channel and to the reference channel preferably so that most of the light passes into the measurement channel. A shutter 4 admits the light alternatingly to the reference fiber 5 and to the excitation fiber 6. The frequency of alternation must be such that the brightness of the lamp and the sensitivity of the detector do not have time to vary to a significant extent during the cycle. This frequency depends on the type and properties of the source of light and of the light detector, and it is usually most appropriately within the range of 1 to 1000 c/s. The light emitted from the sample 7 is collected into the emission fiber 8. The light coming from the emission fiber and that coming from the reference fiber are combined by means of a beam combiner 9 and passed through an emission filter 10 to the light detector 11. When the shutter 4 is in the position in which it admits the light to the reference fiber, the reference value is measured from the light detector 11. This reference value may be used in any way whatsoever known to a person skilled in the art, such as for adjusting the sensitivity of the detector, for dividing the measurement value obtained from the sample, whereby the quotient obtained is the final result, or for adjusting the integration time of the measurement to be made from the sample in accordance with the way in which the reference value differs from the basic reference value measured earlier.

In the measurement system described above, in principle, the accuracy of the measurements depends only on how precisely the fluorescence of the reference fiber remains constant. It is generally known that the fluorescence of substances decreases with an increase in the temperature. In the case of such materials of which the reference fiber can be made, such as, e.g., polymethylmethacrylate, the dependence of fluorescence on the temperature is several tenths of percent per Kelvin degree. Depending on how the temperature changes inside the apparatus during operation and on how precise the apparatus is supposed to be, it may be necessary to thermostat the reference fiber at a constant temperature. This can be accomplished by placing it in a thermostated space or by placing one or several resistor wires following the fiber underneath a common jacket with the fiber, together with a temperature detector, by whose aid the reference fiber is kept at a constant temperature by means of a thermostat 12.

In the example shown in the FIGURE, a separate beam distributor and shutter are used. Equally well it would be possible to use a member that carries out both of these functions at the same time, such as, e.g., a revolving sector mirror.

In the example of the FIGURE, the excitation light is passed into the sample, and the emission light passed out of the sample, by means of optical fibers. Equally well, some other sort of an optical system might be used, such as, e.g., one consisting of lenses or mirrors, or both. In the FIGURE, for the sake of example, such an optical arrangement is used in which the excitation channel and the emission channel are placed at an angle of 90° relative each other, viewed from the sample. It would be equally well possible to use such prior art arrangements in which the excitation channel and the emission channel are placed at the same side of the sample or at opposite sides of same.

The elements of the apparatus as such are otherwise well known for a person skilled in the art.

What is claimed is:

1. A fluorometer comprising in combination a light source, a beam distributor in the path of light from said source for dividing said light into first and second paths, a measurement channel for passing light from said first path, a reference channel for passing light from said second path, means disposed between said beam distributor light paths and said measurement and reference channels for alternately interrupting the passage of said light to said measurement and reference channels, means for positioning a sample in said measurement channel for receiving light from said first path and producing emitted fluorescent light responsive to said received light, a light detector, and means for coupling to said light detector a predetermined bandwidth of light frequencies from both said emitted fluorescent light in said measurement channel and light in said reference channel, characterized in that said reference channel comprises a fiber optic conductor formed at least in part of fluorescent material having sufficient fluorescence when excited by light from said second path to produce a reference standard of fluorescent emission to calibrate said detector.

2. A fluorometer according to claim 1, characterized in that thermostatically controlled means are coupled with said fiber optic conductor for maintaining said fiber optic conductor at a substantially constant temperature.

3. The method of measuring fluorescence within a sample which comprises the steps of alternately passing light from light source through a measurement channel to excite fluorescence in said sample and through a fiber optic conductor formed at least in part of fluorescent material, detecting fluorescent emission from said fiber optic conductor as a reference standard and comparing said reference standard emission with fluorescent emission from said sample to provide a measure of said sample fluorescence.

4. The method according to claim 3, including the step of maintaining constant the temperature of said fiber optic conductor during a measurement.

* * * * *